United States Patent [19]

O'Hara

[11] Patent Number: 5,151,361
[45] Date of Patent: Sep. 29, 1992

[54] HOST CELLS EXPRESSING GIBBON APE LEUKEMIA VIRUS RECEPTOR

[75] Inventor: Bryan M. O'Hara, Pearl River, N.Y.

[73] Assignee: American Cyanamid Company, Wayne, N.J.

[21] Appl. No.: 675,129

[22] Filed: Mar. 25, 1991

Related U.S. Application Data

[63] Continuation of Ser. No. 398,351, Aug. 24, 1989, abandoned.

[51] Int. Cl.$^5$ .......................... C12N 5/06; C12N 5/10; C07K 13/00
[52] U.S. Cl. ................................ 435/240.2; 435/255; 435/69.1; 530/350
[58] Field of Search .................. 530/350, 387; 514/12; 435/255, 252.3, 69.1, 240.2

[56] References Cited

U.S. PATENT DOCUMENTS 4,861,720  8/1989  Pederson et al. .................... 435/238
4,877,729  10/1989  Clark et al. ....................... 435/69.52

OTHER PUBLICATIONS

Wilson et al "Formation of Infectious Hybrid Virions w/GALV and hu Tcell LV Retroviral Env gp and the gag and pol proteins of MoMuLV" J. of Virology 63(5) pp. 2374–3278 (1989).

*Primary Examiner*—David L. Lacey
*Assistant Examiner*—Shelly J. Guest
*Attorney, Agent, or Firm*—Karen A. Lowney

[57] ABSTRACT

The present invention relates to novel purified gibbon ape leukemia receptor proteins and purified DNA sequences encoding these receptor proteins. The invention also relates to a method for identifying receptor proteins using the isolated DNA sequence as a probe, and a method for regulating viral entry into cells by manipulation of the GALV receptor.

2 Claims, 11 Drawing Sheets

FIG. 6A

```
     ----,----+----,----+----,----+----,----+----,----+----,----+
   1 GAGCTGTCCCCGGTGCCGCCGACCCGGGCCGTGCCGTGTGCCCGTGGCTC   50
  51 CAGCCGCTGCCGCCTCGATCTCCTCGTCTCCCGCTCCGCCCTCCCTTTTC  100
 101 CCTGGATGAACTTGCGTCCTTTCTCTTCTCCGCCATGGAATTCTGCTCCG  150
 151 TGCTTTTAGCCCTCCTGAGCCAAAGAAACCCCAGACAACAGATGCCCATA  200
 201 CGCAGCGTATAGCAGTAACTCCCCAGCTCGGTTTCTGTGCCGTAGTTTAC  250
     ----,----+----,----+----,----+----,----+----,----+----,----+
 251 AGTATTTAATTTTATATAATATATATTATTTATTATAGCATTTTTGATAC  300
 301 CTCATATTCTGTTTACACATCTTGAAAGGCGCTCAGTAGTTCTCTTACTA  350
 351 AACAACCACTACTCCAGAGAATGGCAACGCTGATTACCAGTACTACAGCT  400
 401 GCTACCGCCGCTTCTGGTCCTTTGGTGGACTACCTATGGATGCTCATCCT  450
 451 GGGCTTCATTATTGCATTTGTCTTGGCATTCTCCGTGGGAGCCAATGATG  500
     ----,----+----,----+----,----+----,----+----,----+----,----+
 501 TAGCAAATTCTTTTGGTACAGCTGTGGGCTCAGGTGTAGTGACCCTGAAG  550
 551 CAAGCCTGCATCCTAGCTAGCATCTTTGAAACAGTGGGCTCTGTCTTACT  600
 601 GGGGGCCAAAGTGAGCGAAACCATCCGGAAGGGCTTGATTGACGTGGAGA  650
 651 TGTACAACTCGACTCAAGGGCTACTGATGGCCGGCTCAGTCAGTGCTATG  700
 701 TTTGGTTCTGCTGTGTGGCAACTCGTGGCTTCGTTTTGAAGCTCCCTAT  750
     ----,----+----,----+----,----+----,----+----,----+----,----+
 751 TTCTGGAACCCATTGTATTGTTGGTGCAACTATTGGTTTCTCCCTCGTGG  800
 801 CAAAGGGGCAGGAGGGTGTCAAGTGGTCTGAACTGATAAAAATTGTGATG  850
 851 TCTTGGTTCGTGTCCCCACTGCTTTCTGGAATTATGTCTGGAATTTTATT  900
 901 CTTCCTGGTTCGTGCATTCATCCTCCATAAGGCAGATCCAGTTCCTAATG  950
 951 GTTTGCGAGCTTTGCCAGTTTTCTATGCCTGCACAGTTGGAATAAACCTC 1000
```

FIG. 6B

```
        ----,----+----,----+----,----+----,----+----,----+
1001   TTTTCCATCATGTATACTGGAGCACCGTTGCTGGGCTTTGACAAACTTCC  1050
1051   TCTGTGGGGTACCATCCTCATCTCGGTGGGATGTGCAGTTTTCTGTGCCC  1100
1101   TTATCGTCTGGTTCTTTGTATGTCCCAGGATGAAGAGAAAAATTGAACGA  1150
1151   GAAATAAAGTGTAGTCCTTCTGAAAGCCCCTTAATGGAAAAAAGAATAG   1200
1201   CTTGAAAGAAGACCATGAAGAAACAAAGTTGTCTGTTGGTGATATTGAAA  1250
        ----,----+----,----+----,----+----,----+----,----+
1251   ACAACCATCCTGTTTCTGAGGTAGGGCCTGCCACTGTGCCCCTCCAGGCT  1300
1301   GTGGTGGAGGAGAGAACAGTCTCATTCAAACTTGGAGATTTGGAGGAAGC  1350
1351   TCCAGAGAGAGAGAGGCTTCCCAGCGTGGACTTGAAAGAGGAAACCAGCA  1400
1401   TAGATAGCACCGTGAATGGTGCAGTGCAGTTGCCTAATGGGAACCTTGTC  1450
1451   CAGTTCACTCAAGCCGTCAGCAACCAAATAAACTCCAGTGGCCACTCCCA  1500
        ----,----+----,----+----,----+----,----+----,----+
1501   GTATCACACCGTGCATAAGGATTCCGGCCTGTACAAAGAGCTACTCCATA  1550
1551   AATTACATCTTGCCAAGGTGGGAGATTGCATGGGAGACTCCGGTGACAAA  1600
1601   CCCTTAAGGCGCAATAATAGCTATACTTCCTATACCATGGCAATATGTGG  1650
1651   CATGCCTCTGGATTCATTCCGTGCCAAAGAAGGTGAACAGAAGGGCGAAG  1700
1701   AAATGGAGAAGCTGACATGGCCTAATGCAGACTCCAAGAAGCGAATTCGA  1750
        ----,----+----,----+----,----+----,----+----,----+
1751   ATGGACAGTTACACCAGTTACTGCAATGCTGTGTCTGACCTTCACTCAGC  1800
1801   ATCTGAGATAGACATGAGTGTCAAGGCAGCGATGGGTCTAGGTGACAGAA  1850
1851   AAGGAAGTAATGGCTCTCTAGAAGAATGGTATGACCAGGATAAGCCTGAA  1900
1901   GTCTCTCTCCTCTTCCAGTTCCTGCAGATCCTTACAGCCTGCTTTGGGTC  1950
1951   ATTCGCCCATGGTGGCAATGACGTAAGCAATGCCATTGGGCCTCTGGTTG  2000
        ----,----+----,----+----,----+----,----+----,----+
2001   CTTTATATTTGGTTTATGACACAGGAGATGTTTCTTCAAAAGTGGCAACA  2050
2051   CCAATATGGCTTCTACTCTATGGTGGTGTTGGTATCTGTGTTGGTCTGT   2100
2101   GGTTTGGGGAAGAAGAGTTATCCAGACCATGGGGAAGGATCTGACACCGA  2150
2151   TCACACCCTCTAGTGGCTTCAGTATTGAACTGGCATCTGCCCTCACTGTG  2200
2201   GTGATTGCATCAAATATTGGCCTTCCCATCAGTACAACACATTGTAAAGT  2250
        ----,----+----,----+----,----+----,----+----,----+
2251   GGGCTCTGTTGTGTCTGTTGGCTGGCTCCGGTCCAAGAAGGCTGTTGACT  2300
2301   GGCGTCTCTTTCGTAACATTTTTATGGCCTGGTTTGTCACAGTCCCCATT  2350
```

FIG. 6C

```
2351 TCTGGAGTTATCAGTGCTGCCATCATGGCAATCTTCAGATATGTCATCCT 2400
2401 CAGAATGTGAAGCTGTTTGAGATTAAAATTTGTGTCAATGTTTGGGACCA 2450
2451 TCTTAGGTATTCCTGCTCCCCTGAAGAATGATTACAGTGTTAACAGAAGA 2500
     ----,----+----,----+----,----+----,----+----,----+
2501 CTGACAAGAGTCTTTTTATTTGGGAGCAGAGGAGGGAAGTGTTACTTGTG 2550
2551 CTATAACTGCTTTTGTGCTAAATATGAATTGTCTCAAAATTAGCTGTGTA 2600
2601 AAATAGCCCGGGTTCCACTGGCTCCTGCTGAGGTCCCCTTTCCTTCTGGG 2650
2651 CTGTGAATTCCTGTACATATTTCTCTACTTTTTGTATCAGGCTTCAATTC 2700
2701 CATTATGTTTAATGTTGTCTCTGAAGATGACTTGTGATTTTTTTTTCTT 2750
     ----,----+----,----+----,----+----,----+----,----+
2751 TTTTTTAAACCATGAAGAGCCGTTTGACAGAGCATGCTCTGCGTTGTTGG 2800
2801 TTTCACCAGCTTCTGCCCTCACATGCACAGGGATTTAACAACAAAAATAT 2850
2851 AACTACAACTTCCCTTGTAGTCTCTTATATAAGTAGAGTCCTTGGTACTC 2900
2901 TGCCCTCCTGTCAGTAGTGGCAGGATCTATTGGCATATTCGGGAGCTTCT 2950
2951 TAGAGGGATGAGGTTCTTTGAACACAGTGAAAATTTAAATTAGTAACTTT 3000
     ----,----+----,----+----,----+----,----+----,----+
3001 TTTGCAAGCAGTTTATTGACTGTTATTGCTAAGAAGAAGTAAGAAAGAAA 3050
3051 AAGCCTGTTGGCAATCTTGGTTATTTCTTTAAGATTTCTGGCAGTGTGGG 3100
3101 ATGGATGAATGAAGTGGAATGTGAACTTTGGGCAAGTTAAATGGGACAGC 3150
3151 CTTCCATGTTCATTTGTCTACCTCTTAACTGAATAAAAAAGCCTACAGTT 3200
3201 TTTAGAAAAAA                                        3220
```

FIG. 7

```
  1 Met Ala Thr Leu Ile Thr Ser Thr Ala Ala Ser   15
 16 Gly Pro Leu Val Asp Tyr Leu Trp Met Leu Gly Phe Ile   30
 31 Ile Ala Phe Val Leu Ala Phe Ser Val Gly Ala Asn Asp Val Ala   45
 46 Asn Ser Phe Gly Thr Ala Val Gly Ser Gly Val Val Thr Leu Lys   60
 61 Gln Ala Cys Ile Leu Ala Ser Ile Phe Glu Thr Val Gly Ser Val   75
                                   +
 76 Leu Leu Gly Ala Lys Val Ser Glu Thr Ile Arg Lys Gly Leu Ile   90
 91 Asp Val Glu Met Tyr Asn Ser Thr Gln Gly Leu Leu Met Ala Gly  105
106 Ser Val Ser Ala Met Phe Gly Ser Ala Val Trp Gln Leu Val Ala  120
121 Ser Phe Leu Lys Leu Pro Ile Ser Gly Thr His Cys Ile Val Gly  135
136 Ala Thr Ile Gly Phe Ser Leu Val Ala Lys Gly Gln Glu Gly Val  150
                                   +
151 Lys Trp Ser Glu Leu Ile Lys Ile Val Met Ser Trp Phe Val Ser  165
166 Pro Leu Leu Ser Gly Ile Met Ser Gly Ile Leu Phe Phe Leu Val  180
181 Arg Ala Phe Ile Leu His Lys Ala Asp Pro Val Pro Asn Gly Leu  195
196 Arg Ala Leu Pro Val Phe Tyr Ala Cys Thr Val Gly Ile Asn Leu  210
211 Phe Ser Ile Met Tyr Thr Gly Ala Pro Leu Leu Gly Phe Asp Lys  225
                                   +
226 Leu Pro Leu Trp Gly Thr Ile Leu Ile Ser Val Gly Cys Ala Val  240
241 Phe Cys Ala Leu Ile Val Trp Phe Phe Val Cys Pro Arg Met Lys  255
256 Arg Lys Ile Glu Arg Glu Ile Lys Cys Ser Ser Pro Ser Glu Pro  270
271 Leu Met Glu Lys Lys Asn Ser Leu Lys Glu Asp His Glu Thr  285
286 Lys Ser Leu Val Gly Asp Ile Glu Asn Lys His Pro Val Ser Glu  300
```

FIG. 7 (cont.)

```
301 Val Gly Pro Ala Thr Val Pro Leu Gln Ala Val Val Glu Glu Arg  315
316 Thr Val Ser Phe Lys Leu Gly Asp Leu Lys Glu Glu Pro Glu Arg  330
331 Glu Arg Leu Pro Ser Val Asp Gln Val Glu Glu Thr Ser Ile Asp  345
346 Ser Thr Val Asn Gly Ala Val Gln Leu Pro Asn Gly Asn Leu Val  360
361 Gln Phe Ser Gln Ala Val Ser Asn Gln Ile Asn Ser Ser Gly His  375
                                                   +
376 Ser Gln Tyr His Thr Val His Lys Asp Ser Gly Leu Tyr Lys Glu  390
391 Leu Leu His Lys Leu His Leu Ala Lys Val Gly Asp Cys Met Gly  405
406 Asp Ser Gly Asp Lys Pro Leu Arg Arg Asn Asn Ser Tyr Thr Ser  420
421 Tyr Thr Met Ala Ile Cys Gly Met Pro Leu Asp Ser Phe Arg Ala  435
436 Lys Glu Gln Gly Leu Gly Gly Met Glu Gln Lys Leu Leu Thr Trp  450
                   —
451 Pro Asn Ala Asp Ser Lys Arg Ile Arg Met Asp Ser Tyr Thr      465
466 Ser Tyr Cys Asn Ala Val Ser Asp Leu His Ser Ala Ser Glu Ile  480
481 Asp Met Ser Val Lys Ala Met Gly Leu Gly Asp Arg Lys Gly      495
496 Ser Asn Gly Ser Leu Glu Glu Trp Tyr Asp Asp Lys Pro Glu      510
511 Val Ser Leu Leu Phe Gln Ile Leu Gln Ile Leu Thr Ala Cys Phe  525
                                                   +
526 Gly Ser Phe Ala His Gly Leu Asn Asp Val Ser Asn Ala Ile Gly  540
541 Pro Leu Val Ala Leu Tyr Val Tyr Asp Thr Gly Asp Val Ser      555
556 Ser Lys Val Ala Thr Pro Ile Trp Leu Leu Tyr Gly Gly Val      570
571 Gly Ile Cys Val Gly Ser Leu Trp Val Trp Gly Arg Arg Val Ile Gln  585
586 Thr Met Gly Lys Asp Leu Thr Pro Ile Thr Pro Ser Ser Gly Phe  600
                   —
601 Ser Ile Glu Leu Ala Ser Ala Leu Thr Val Val Ile Ala Ser Asn  615
616 Ile Gly Leu Pro Ile Ser Thr Thr His Cys Lys Val Gly Ser Val  630
631 Val Ser Val Gly Trp Leu Arg Ser Lys Lys Ala Val Asp Trp Arg  645
646 Leu Phe Arg Asn Ile Phe Met Ala Trp Phe Val Thr Val Pro Ile  660
661 Ser Gly Val Ile Ser Ala Ala Ile Met Ala Ile Phe Arg Tyr Val  675
                   —
676 Ile Leu Arg Met Ter                                          680
```

HOST CELLS EXPRESSING GIBBON APE LEUKEMIA VIRUS RECEPTOR

This is a continuation of co-pending application Ser. No. 07/398,351 filed on Aug. 24, 1989, now abandoned.

BACKGROUND OF THE INVENTION

The present invention relates to the receptor protein for gibbon ape leukemia virus, a retrovirus and to animal genes and their proteins which interact with gibbon ape leukemia virus (GALV). These GALV receptor proteins are required for entry of the virus into cells, and are therefore defined as cellular receptors for GALV.

Retroviruses can be placed into specified groups depending on the pathway used by the viruses to enter cells. It is thought that members of one given group utilize specific cellular receptors for entry into cells and that there is little, if any, cross-utilization of receptors by members of different groups. In general, these receptors have remained virtually unexplored. Of the approximately eight human receptors specific for the retroviruses known to infect human cells, only one has been cloned (CD4 for HIV; Maddon et al., 1986; McDougal et al., 1986). This invention therefore relates to one of the currently known receptors required for infection of animals, specifically human cells, by a retrovirus. Although the presence of a specific receptor protein for GALV (and for other retroviruses utilizing other receptor pathways) has been speculated, no GALV-specific receptor has heretofore been cloned or characterized.

While mention has been made of GALV, it is understood that simian sarcoma-associated virus and other viruses as stated above, utilize the same receptor (Weiss et al., 1984).

The novel genes and proteins of the present invention are useful in experimental manipulation of the GALV host, in analysis of virus/receptor interactions, and in elucidation and exploitation of the normal role of the receptor, which include functions in immune activity.

BRIEF DESCRIPTION OF THE DRAWINGS

FIG. 6-6A,C. LDNA sequence of the human cDNA for the GALV receptor. The long open reading frame extends from positions 371 to 2407, inclusively.

FIG. 7. Amino acid sequence of the human GALV receptor protein, as derived from the long open reading frame in FIG. 6.

SUMMARY OF THE INVENTION

Figure 4:
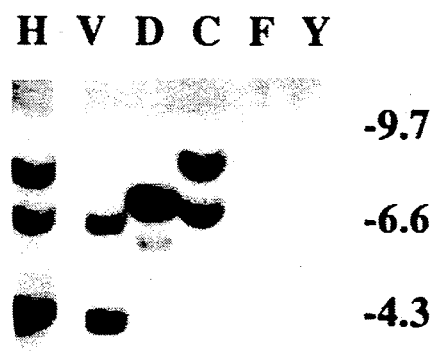
FIG. 4. Southern analysis of EcoRI-digested human (H), African green monkey vero cell (V), dog (D), cat (C), frog (F) and yeast (Y) DNAs using the 5' EcoRI insert fragment of lambda HGR6 (subcloned in pUC118) as probe.

The present invention relates to the GALV protein receptor and its homologs expressed in a wide variety of animal tissues. The primary amino acid sequence of the receptor is illustrated in FIG. 7, in which the human receptor is shown. However, as would be expected from the wide host range of GALV (Weiss et al., 1984) and from Southern analysis of species other than human (FIG. 4), closely-related homologs exist in species such as dog, cat, mouse and monkey, and others. These observations support the universal existence of discrete genes truly homologous to the human GALV receptor. Thus, the present invention relates not only to the specific protein identified in FIG. 7, but also to proteins having substantially the same amino acid sequence and substantially the same capacity to all to allow viral infection as the protein illustrated in FIG. 7. Further, the invention relates to the purified DNA sequence (FIG. 6-6A coding for the (human) GALV receptor and to DNAs having substantially the same DNA sequence with substantially the same amino acid coding sequence DNA as in FIG. 6-6A. It is appreciated by those of ordinary skill in the art that other such proteins from other species, as well as other alternatives to the protein illustrated in FIG. 7, are isolated by the process of the present invention. Various expression systems may be used to produce varieties to these proteins but such varieties still result in a protein with similar biological activities to the present protein. It is also recognized to those skilled in the art that modifications to the DNA sequence presented in FIG. 6 results in GALV receptor proteins. The resultant DNA sequences and resulting proteins having substantially the same role in allowing viral entry are included within the scope of the invention. The biological function of the receptor is measured by infection studies of cells normally not infectable and transfected with constructs designed to express the protein (as demonstrated in Table 1). Further, antibody binding studies characterize and identify amino acid sequence and structure. Virus infection studies functionally identify a protein's role in allowing viral entry.

The GALV receptor proteins of the present invention are produced through expression vectors comprising a DNA sequence encoding a human GALV receptor protein (or DNA sequences of the homologs of other species) or mutants (with or without the ability to confer susceptibility to infection on normally uninfectable cells) wherein one or more amino acids have been inserted, deleted, or substituted in or from the amino acid sequence of the human GALV receptor protein or of its homologs from other species.

Additionally, the present invention includes a method for identifying GALV receptor homologs of all animal species wherein a DNA probe selected from the DNA in FIG. 6-6A or with substantially the same DNA sequence as that identified in FIG. 6-6A is used to isolate the appropriate DNA from the other species.

Further, as can be determined by those skilled in the art, the manipulation of the GALV receptor allows for regulation of viral entry into cells. This allows the prevention of certain viral infections and the ability to control this mechanism for retroviruses utilizing the GALV receptor protein for cellular entry. A GALV-receptor protein regulation amount of a GALV-receptor protein-infecting agent is used to manipulate cellular infectivity for retroviruses.

For purposes of the present invention, the plasmids, DNA sequences, and microorganisms deposited in connection with the present invention, except where specified to the contrary, are deposited in American Cyanamid Company's culture collection maintained in Princeton, N.J., and are deposited with American Type Culture Collection in 12301 Parklawn Drive, Rockville, Md. 20952 USA on Aug. 2, 1989.

Although the use of genetic engineering techniques lend themselves to effective methods to produce the GALV receptor proteins of the present invention, it is equally to be noted that the present proteins encompass other methods of production, such as chemical synthesis or purification from animal tissues.

It is an object of the present invention, therefore to provide the novel receptor protein of the GALV receptor. Also, the GALV receptor protein of other animal species, besides the human GALV receptor protein, is encompossed by the present invention. Another object of the invention is to provide an isolated DNA sequence coding for the GALV receptor. These and other objects of the invention will become apparent by the more detailed description of the invention provided hereinbelow.

DETAILED DESCRIPTION OF THE INVENTION

The present invention relates to the GALV receptor protein. The species analyzed in greatest detail is the human, although it is recognized that similar proteins exist in other animal species. Therefore, the invention includes those homologous proteins from other species The present invention discloses the structure of cDNA for the GALV receptor from human HL60 cells. Further, the functionality of the isolated cDNA in allowing viral entry is provided in the following examples but is not limitative thereof.

EXAMPLE 1

Isolation Of GALV Receptor

Portions of the human receptor gene for gibbon ape leukemia virus (GALV) are isolated in the following manner. Firstly, DNA from human cells (which are easily infected with GALV and therefore express that viral receptor) are introduced into mouse N1H3T3 cells (which cannot be infected with the virus) in one of a variety of ways, the procedure of $CaPO_4$ precipitation being described below. High molecular weight human DNA is mixed with pSV2gpt in aqueous solution containing $CaCl_2$ and the mixture is added to a second solution containing phosphate and HEPES buffer at pH 7.1. The DNAs precipitate together in aggregates with $CaPO_4$ and this aggregate is applied to cells in culture (mouse N1H3T3 cells). A portion of the cells takes up aggregates of the DNA mixture and incorporates and expresses the transfected DNA.

In order to study only those cells which have been transfected, selection is imposed for the presence of pSV2gpt. To do this, cells are grown in medium containing mycophenolic acid and xanthine. The mycophenolic acid imposes a metabolic block on the cells which can be overcome by the expression of guanosyl phoribosyltransferase (encoded by pSV2gpt) through its utilization of xanthine (Mulligan and Berg, 1981). After about two weeks in this medium, only transfected cells remain. A given cell in this culture now expresses approximately 0.1% of the human donor DNA. A portion of these (approximately 1/1000) are expected to express the human receptor for GALV. Such cells are isolated by infection with an antibiotic-resistant virus which requires interaction with the GALV receptor to enter cells. This virus is made by rescuing pGV16, a G418-resistant, replication-defective virus (Noda et al., 1986) from cells, using GALV, such that the pGV16 virus is pseudotyped by GALV. Supernatant from these infected cells now contains GALV and pGV16 pseudotyped by GALV (i.e., the pGV16 RNA genome is contained in a GALV particle). The mixture [termed pGV16(GALV)] can now only infect cells using the pathway regularly used by GALV. This mixture is applied to the transfected mouse cells and these are treated two days later with G418 antibiotic. Only cells infected with pGV16 survive. These are termed primary transfectants and should contain approximately 0.1% of the human genome in each independent isolate.

EXAMPLE 2

Transfection

The transfected material found in the primary transfectants will contain a large amount of human repetitive sequences and should also include the human GALV receptor gene. However, because the pressure for the maintenance of the gene is lost after infection with virus and selection for pGV16, many transfectants can be expected to have segregated the gene, as is normal for any such experiment. For this reason, a primary transfectant is sought which has been infected with pGV16 but not with the replication competent GALV. The continued presence of the receptor, and therefore of the receptor gene, can be demonstrated in such a cell because it is not immune to superinfection as are cells which have been infected with GALV. These constitute the majority of isolates because GALV is in excess over pGV16 in the pGV16(GALV) stocks. A transfectant infected only with pGV16 is chosen, in this case the cell termed GRT5, DNA is prepared from it, and the DNA used in a second round of transfection to obtain secondary transfectants. The process to obtain these is similar to that used to derive primary transfectants. That is, DNA from GRT5 is mixed with pSV2gpt, precipitated with $CaPO_4$, and transfected into NIH3T3 cells. These are then grown in medium containing mycophenolic acid and xanthine and the surviving cells are infected with pGV16(GALV). G418 is then applied and surviving cells are grown up and examined to identify presumptive secondary transfectants for the receptor gene. Since proviral pGV16 is present in the primary donor DNA, some of the secondary transfectants will have become G418-resistant from transfection of the proviral DNA. The bona fide receptor transfectants can, however, be distinguished from these because the majority of the secondary transfectants should be GALV producers. The secondary transfectants are therefore screened for GALV production and DNA is prepared from any found. This DNA is analyzed in Southern analysis to determine if any of the producers contain human repetitive sequences. Because the processes of primary and secondary transfection successively reduce the amount of human repetitive DNA to be found in a transfectant, it is expected that any repetitive human DNA found in a secondary transfectant is specifically associated with the receptor gene.

EXAMPLE 3

Isolation of cDNA and cDNA Probes

Figure 1:
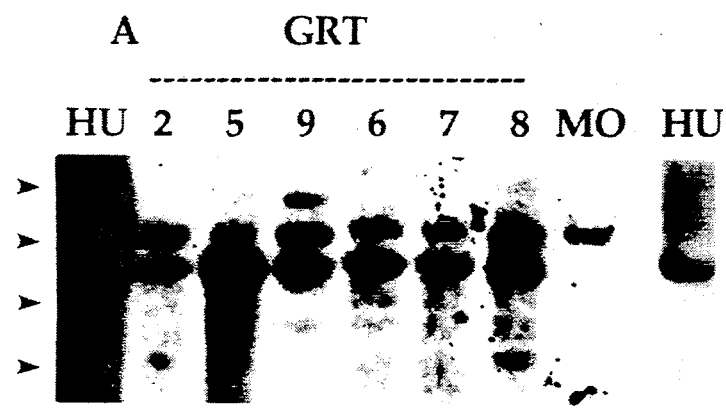
FIG. 1. Southern analysis of human (HU), transfectant (GRT), and mouse (MO) BamHI-digested DNAs. The left panel shows a blot hybridized with the entire (repeat-containing) 3.5 kb EcoRI insert of pR7h. The right lane is hybridized with the 2.2 kb EcoRI-HindIII subfragment.

A genomic library is constructed from any such secondary transfectants found in Example 2(in this case GRT9, the secondary transfectant, and lambda gt10 and EcoRI as the vector and cloning enzyme, respectively) and screened for the presence of clones containing human repetitive DNA using human DNA made radioactive in nick translation as probe. One in 500,000 clones is found to hybridize with the probe. This clone (lambda R7h) is plaque-purified to homogeneity and its 3.5 kb EcoRI insert is cloned in pGEM2 and pUC118. This 3.5 kb EcoRI fragment is found to consist of 2.2 and 1.3 kb EcoRI-HindIII fragments. Use of the entire 3.5 kb fragment as probe in Southern analysis demonstrates that the cloned DNA contains human repetitive sequences, as expected, and that it hybridizes to a 6.6 kb EcoRI fragment in most of the transfectants but not appreciably to mouse DNA (FIG. 1, longer exposure times reveal the presence of a hybridizing band in mouse DNA representing the murine homology, as expected). The presence of this latter transfected sequence in independent transfectants demonstrates that the sequences in lambda R7h are part of or are in close proximity to the receptor gene. Use of the 2.2 kb fragment as probe gives the same result except that in human DNA only a single fragment of 6.6 kb is detected (FIG. 1). This indicates that only single copy sequences are contained in this fragment.

Figure 2:
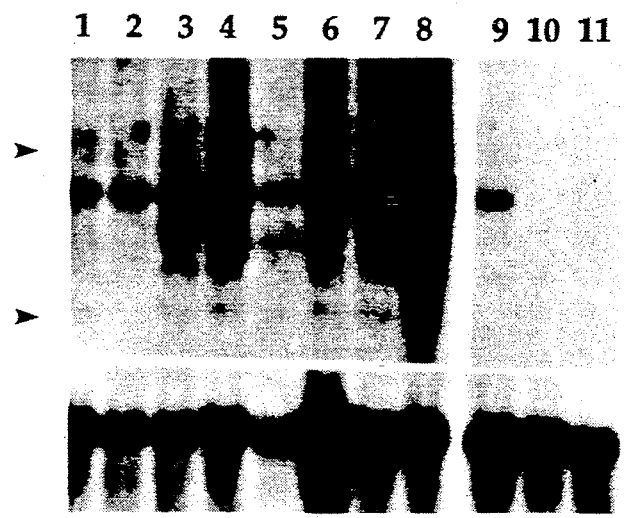
FIG. 2. Northern analysis of human, transfectant, and mouse RNAs. Probes used are the 2.2 kb EcoRI-HindIII subfragment of pR7h (upper panel) and an actin probe (lower panel; O'Hara et al., 1987). Lanes 1-4, total cellular oligo-dT purified RNA of the human cell line TU1.1.1 (O'Hara et al., 1987). Lane 1, confluent cells. 2, log-phase. 3, confluent GALV-infected. 4, confluent Mo-MuSV(GALV)-infected. Lanes 5-8, total cellular oligo-dT purified RNA of the human cell line NT2.1.1 (O'Hara et al., 1987). Lane 5, confluent. 6, log-phase. 7, confluent GALV-infected. 8, confluent Mo-MuSV(GALV)- infected. 9-11, cytoplasmic oligo-dT purified RNAs of primary transfectant GRT5, secondary transfectant GRT9, and NIH3T3 cells, resp.
Figure 5:
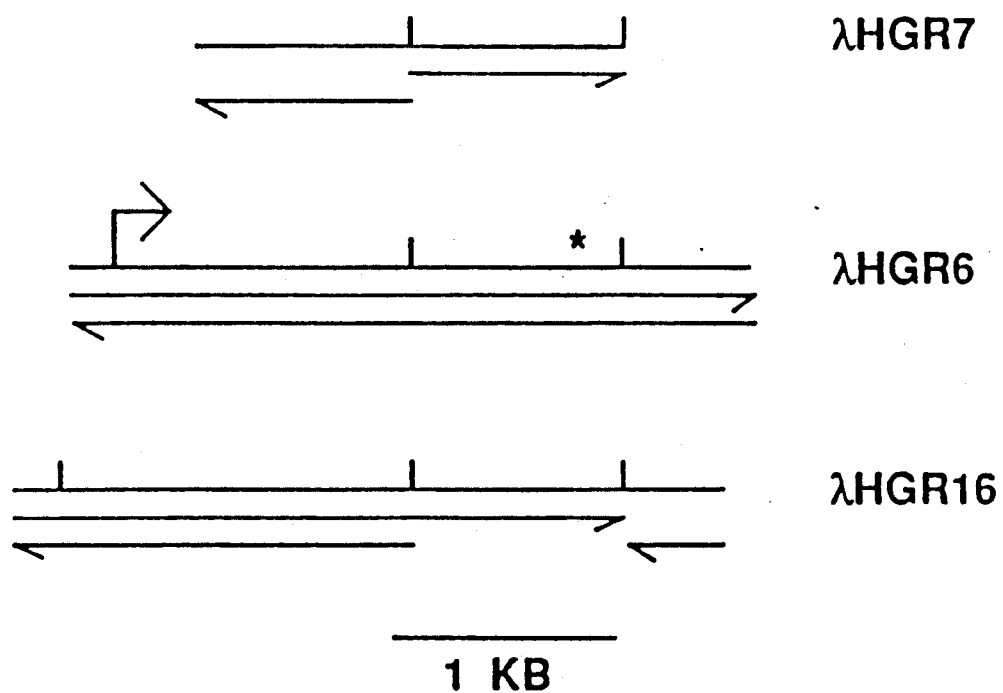
FIG. 5. Human cDNAs isolated and the strands sequenced. Notches represent EcoRI sites. EcoRI linkers are present at each end of each clone where no notch is indicated. The long open reading frame is indicated for lambda HGR6 by the arrow (translation start) and asterisk (termination codon).

When this fragment is used as probe in northern analysis, a single mRNA of approximately 4 kb is detected in human cells and in GRT5, the transfectant with the highest copy number for the transfected DNA; no strongly hybridizing RNA is found in mouse cells (FIG. 2). This indicates that the cloned sequences are expressed in RNA and are therefore suitable for screening cDNA libraries. Accordingly, a cDNA library from human HL60 cells (obtained from Clontech, #HL1020b) is screened with the fragment and 1/10,000 plaques are found to hybridize. Three of these (lambda isolates HGR6, HGR7, and HGR16, FIG. 5) are purified and the EcoRI fragments contained are subcloned in pUC118 and sequenced using the dideoxy termination method.

Analysis of the sequences reveals several features.

1) The sequences of the clones are virtually identical.

2) Lambda HGR6 and lambda HGR16 contain a single large open reading frame of 679 amino acids each, the presumptive amino acid sequences of which are identical.

3) Lambda HGR7 appears to be a truncated cDNA in that it contains a large open reading frame with an identical presumptive amino acid sequence for the 3' two-thirds of the presumptive protein encoded by the above isolates starting at amino acid 180 in FIG. 7.

4) The presumptive protein encoded by these isolates (FIG. 7) has the characteristics of an integral membrane protein. That is, analysis by the program of Kyte and Doolittle (1982) indicates several regions as possible membrane-spanning domains (these are approximately residues 15–39, 159–182, 228–251, and 651–674) Other regions are also hydrophobic, though to a lesser degree, and may also represent membrane-spanning domains (for example, regions 56–79, 118–141, and 555–578). The similarity of the presumed protein to integral membrane proteins is in keeping with its expected function as a retroviral receptor.

Figure 3A:
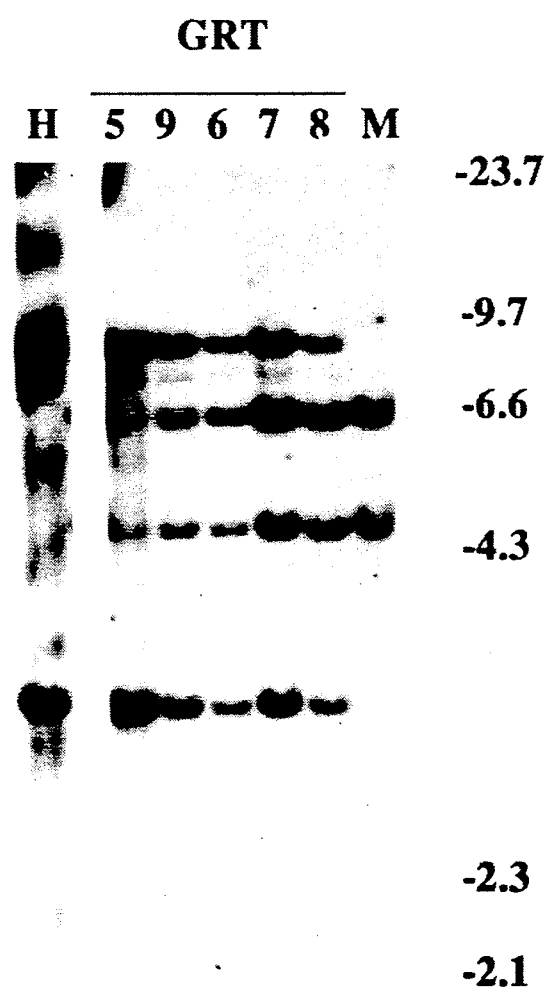
FIGS. 3A-3C. Southern and Northern analysis using cDNA probes. (A) Southern analysis of HindIII-digested human (H), transfectant (GRT), and mouse NIH3T3 (M) DNAs using the 5' EcoRI insert fragment of lambda HGR6 (subcloned in pUC118) as probe. (B) Southern analysis of EcoRI-digested DNAs using the middle EcoRI fragment of lambda HGR6 (subcloned in pUC118) as probe. (C) Northern analysis of oligo-dT-purified RNAs. Lane 1, NT2.1.1 RNA hybridized with a single-standard RNA probe derived from the 5' EcoRI fragment of lambda HGR6 and transcribed in the 3'-5' direction as indicated in FIG. 6. Lane 2 and 3 GRT-5 and NT2.1.1 RNAs hybridized with the three EcoRI inserts of lambda HGR6 (subcloned in pUC118) as probe.
Figure 3B:
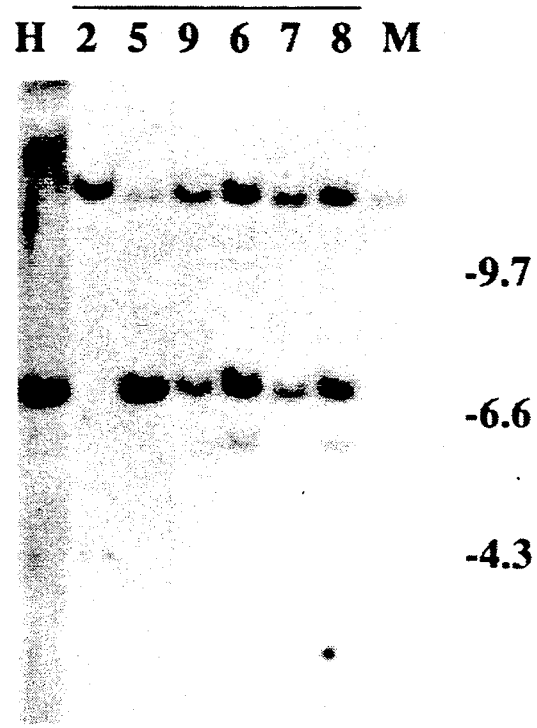
Figure 3C:
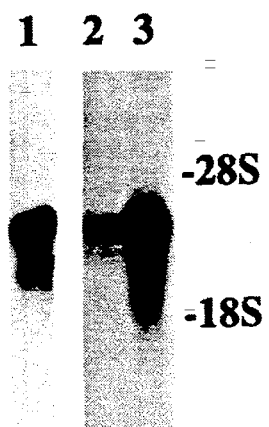

To further characterize the isolates, EcoRI fragments subcloned from lambda HGR6 are used in Southern analysis of human, transfectant and mouse DNAs. It is found that all fragments detected in human DNA are also found in transfectant DNAs but not in mouse DNA (FIG. 3A, B). This further confirms that the isolates are derived from the receptor gene because such a great length of sequence would not be found in independent transfectants unless its presence had been selected for. FIG. 3C shows that the expected RNA is detected using cDNA probes.

EXAMPLE 4

Expression

Figure 8:
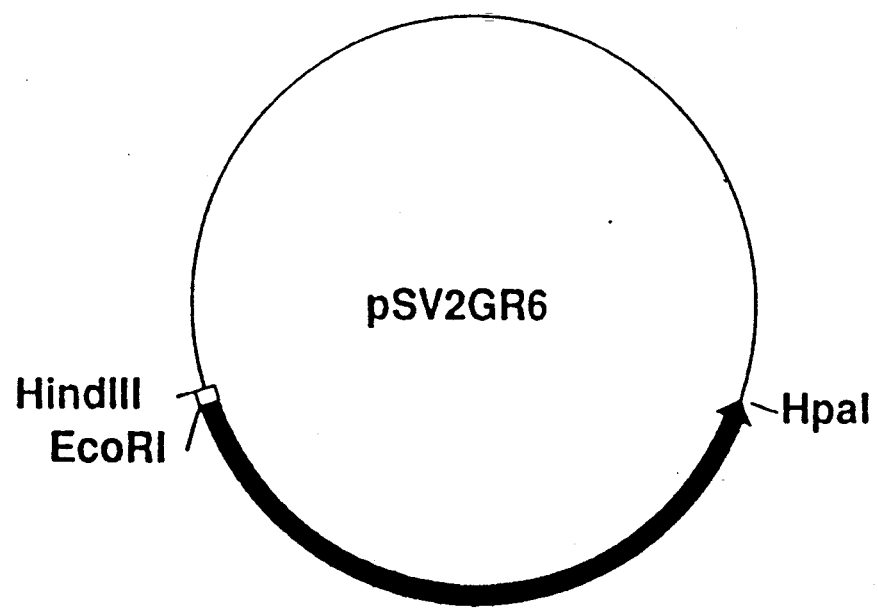
FIG. 8. Structure of pSV2GR6. The thin black line represents sequences derived from pSV2gpt the small box represents sequences derived from the multiple cloning site of pUC118, and the arrowed box represents sequences derived from the insert of lambda HGR-6. For this construction, lambda HGR6 is digested partially with EcoRI and the three contiguous EcoRI inserts are isolated as a single fragment. This is then cloned at the EcoRI site in pUC118 (to give pHGR6-1), so that the presumed 5' end of the insert is proximal to the HindIII site in pUC118. The portion of this plasmid between the HindIII and HpaI sites is cloned between the HindIII and HpaI sites of pSV2gpt to give pSV2GR6.

The ultimate proof that lambda HGR6 encodes the GALV receptor is derived by demonstrating its potential to confer susceptibility to GALV infection on mouse cells. pHGR6-1, containing the three EcoRI insert fragments of lambda HGR6 in the proper orientation, is digested with HindIII, which cuts in the multiple cloning site of the pUC118 vector at the 5' end of the insert, and with HpaI, which cuts in the 3' untranslated region of the insert. This fragment is used to replace the region of pSV2gpt between the HindIII and HpaI sites. The resulting plasmid, pSV2GR6 (FIG. 8), contains the entire open reading frame encoding the receptor with the SV40 early promoter upstream and an SV40 polyadenylation signal downstream. Mouse cells transfected with this plasmid are rendered susceptible to GALV infection, providing final confirmation that the clone does in face encode the GALV receptor. Using the infectious center assay, up to 1% of the cells transfected with pSV2gpt and pSV2GR6 and selected for the presence of pSV2gpt are found to be infectable.

The plasmid pSV2GR6 is deposited in the American Type Culture Collection as deposit number ATCC 68070 (Aug. 2, 1989).

TABLE I

Expression of pSV2GR6 renders mouse NIH3T3 cells susceptible to infection by GALV

| DNA Transfected | IC[a] | G418[R] colonies[b] | |
|---|---|---|---|
| | | No virus | pGV16 (GALV) |
| pSV2gpt | $0/10^5$ | ND | $0/10^6$ |
| pSV2gpt + pSV2GR6 | $739/10^5$ | $0/10^7$ | $252/6 \times 10^6$ |

[a]Number of cells producing virus/number tested. NIH3T3 cells (transfected and then grown in medium containing mycophenolic acid) were exposed to pGV16 (GALV) and plated with PG4 cells in an infectious center assay.
[b]Colonies formed in medium containing G418/number tested. NIH3T3 cells (transfected and then grown in medium containing mycophenolic acid) were plated in the presence of G418 after exposure, where indicated, to pGV16 (GALV).
ND = not done.

BIBLIOGRAPHY

Kyte J and Doolittle RF. A simple method for displaying the hydropathic character of a protein. *Journal of Molecular Biology*, 157 105–132 (1982).

Maddon PJ, Dalgleish AG, McDougal JS, Clapham PR, Weiss RA, and Axel R. The T4 gene encodes the AIDS virus receptor and is expressed in the immune system and the brain. *Cell*, 47:333–348 (1986).

McDougal JS, Kennedy MS, Sligh JM, Cort SP, Mawle A, and Nicholson JKA. Binding of HTLV-III/LAV to T4+cells by a complex of the 110K viral protein and the T4 molecule. *Science*, 231:382–385 (1986).

Mulligan RC and Berg P. *Proceedings of the National Academy of Sciences, USA*, 78:2072–2076 (1981).

Noda TM, Satake M, Robins T, and I to Y. Isolation and characterization of NIH3T3 cells expressing polyoma small T antigen. *Journal of Virology*, 60:105–113 (1986).

O'Hara B, Klinger HP, Curran T, Zhang Y, and Blair DG. *Molecular and Cellular Biology*, 7:2941–2946 (1987).

Southern PJ and Berg P. Journal of Molecular and Applied *Genetics*, 1:327–341 (1982).

Weiss RN, Teich N, Varmus H, and Coffin J. RNA Tumor Viruses: Molecular Biology of Tumor Viruses, Second Edition, Volume 1. Cold Spring Harbor Laboratories, Cold Spring Harbor 1984.

What is claimed is:

1. A non-human mammalian or yeast host cell expressing a human GALV receptor protein.

2. A non-human mammalian or yeast host cell expressing a GALV receptor protein having the amino acid sequence defined in FIG. 7.

* * * * *